(12) United States Patent
François

(10) Patent No.: US 8,994,956 B2
(45) Date of Patent: Mar. 31, 2015

(54) OPTICAL DEVICE FOR OBSERVING MILLIMETRIC OR SUBMILLIMETRIC STRUCTURAL DETAILS OF AN OBJECT WITH SPECULAR BEHAVIOUR

(75) Inventor: Becker François, Lyons (FR)

(73) Assignee: Signoptic Technologies, Le Bourget du Lac (FR)

( * ) Notice: Subject to any disclaimer, the term of this patent is extended or adjusted under 35 U.S.C. 154(b) by 457 days.

(21) Appl. No.: 12/740,193

(22) PCT Filed: Oct. 29, 2008

(86) PCT No.: PCT/EP2008/064683
§ 371 (c)(1),
(2), (4) Date: Apr. 28, 2010

(87) PCT Pub. No.: WO2009/056571
PCT Pub. Date: May 7, 2009

(65) Prior Publication Data
US 2010/0231894 A1  Sep. 16, 2010

Related U.S. Application Data

(60) Provisional application No. 61/006,441, filed on Jan. 14, 2008.

(30) Foreign Application Priority Data

Oct. 29, 2007 (FR) ...................... 07 58664

(51) Int. Cl.
*G01B 11/24* (2006.01)
*G01B 11/25* (2006.01)
(Continued)

(52) U.S. Cl.
CPC .......... *G01B 11/2509* (2013.01); *G01B 11/306* (2013.01); *G01N 21/55* (2013.01); *G01N 21/95* (2013.01)
USPC ......................................... 356/601; 356/612

(58) Field of Classification Search
CPC .... G01B 11/24; G01B 11/2509; G01B 11/25; G01B 11/30; G01B 11/303; G01B 11/306; G01N 21/55; G01N 2021/555; G01N 2021/558; G01N 2021/559; G01N 21/95; G01N 21/956; G01N 21/958
USPC ................................................... 356/600–640
See application file for complete search history.

(56) References Cited

U.S. PATENT DOCUMENTS 3,782,827 A * 1/1974 Nisenson et al. ............. 356/600
3,912,922 A * 10/1975 Lacotte et al. ................ 250/204
(Continued)

FOREIGN PATENT DOCUMENTS

EP    1726914    11/2006
FR    2285990    4/1976
(Continued)

OTHER PUBLICATIONS http://www.merriam-webster.com/dictionary/conjugate.*
(Continued)

*Primary Examiner* — Tarifur Chowdhury
*Assistant Examiner* — Michael P Lapage
(74) *Attorney, Agent, or Firm* — Clark & Brody

(57) ABSTRACT

A device for observation, by reflection, of the structural details of an object (2) that exhibits a behavior that is at least partially specular, located in an exposure area, which includes: at least one radiation source with an emission surface (6) possessing at least two distinct zones (26, 27) emitting streams of radiation, where at least one of the characteristics differs from one zone to the next; an optical projection system that is located in line with the radiation source in relation to the exposure zone, in the path of the radiation; an optical exposure system (18) designed to optically link the entry aperture (14) of the optical projection system and the emission surface (6); a projection surface (10) that is linked optically with the object in the exposure zone, and whose received radiation depends on the deflection on the object (2).

17 Claims, 6 Drawing Sheets

(51) Int. Cl.
*G01B 11/30* (2006.01)
*G01N 21/55* (2014.01)
*G01N 21/95* (2006.01)

(56) References Cited

U.S. PATENT DOCUMENTS

| | | | |
|---|---|---|---|
| 4,030,830 A * | 6/1977 | Holly | 356/489 |
| 5,991,040 A * | 11/1999 | Doemens et al. | 356/614 |
| 2002/0001029 A1 | 1/2002 | Abe | |
| 2002/0134839 A1 | 9/2002 | Iwaki | |
| 2003/0026475 A1 | 2/2003 | Yahashi et al. | |
| 2004/0213463 A1 | 10/2004 | Morrison | |
| 2005/0262350 A1 | 11/2005 | Boutant | |
| 2006/0050284 A1 | 3/2006 | Bertin-Mourot et al. | |
| 2006/0114464 A1* | 6/2006 | Klingenberg et al. | 356/437 |
| 2008/0186512 A1* | 8/2008 | Kee et al. | 356/610 |

FOREIGN PATENT DOCUMENTS

| | | |
|---|---|---|
| FR | 2817042 | 5/2002 |
| FR | 2866139 | 8/2005 |
| FR | 2870376 | 11/2005 |
| WO | 2005/076651 | 8/2005 |

OTHER PUBLICATIONS

Keating, Geometric, physical and visual optics, 2002, Butterworth-Heinemann, pp. 34-36.*

Hecht, Optics, 2002, Pearson, Addison, Wesley, pp. 149-150.*

B. Gilbert et al., "Multicolor fringe projection system with enhanced 3-D reconstruction of surfaces", Part of the SPIE Conference on Three-Dimensional Imaging, Optical Metrology, and Inspection IV, Boston, MA, Nov. 1998, SPIE vol. 3520, pp. 13-20.

* cited by examiner

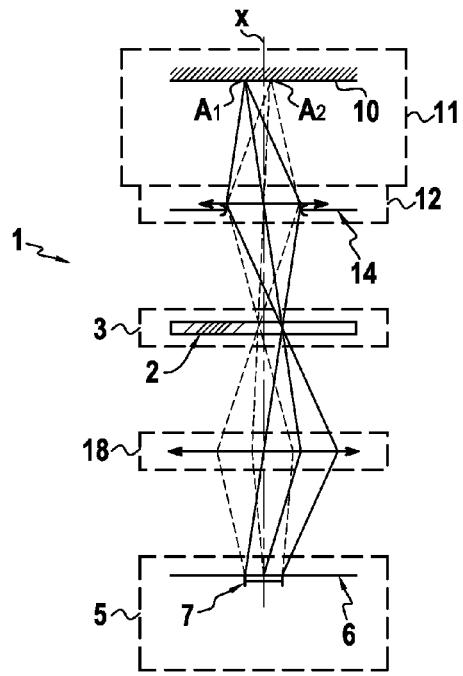
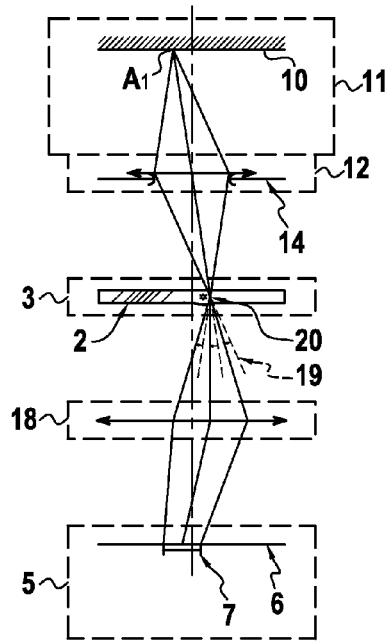
FIG.1         FIG.1A
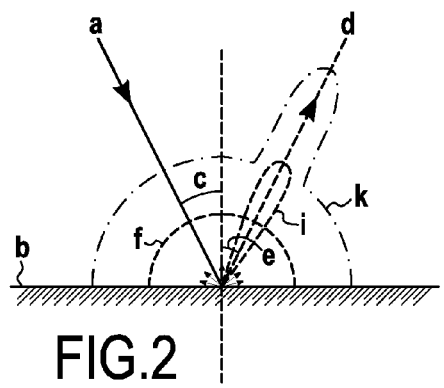
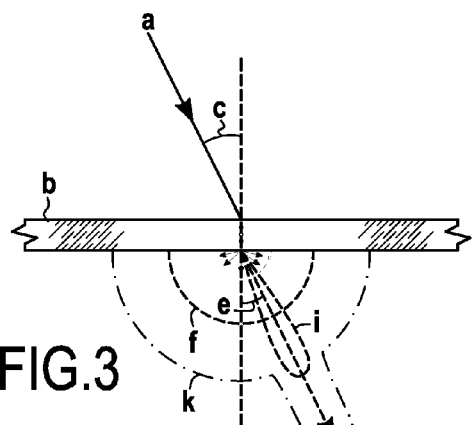
FIG.2         FIG.3
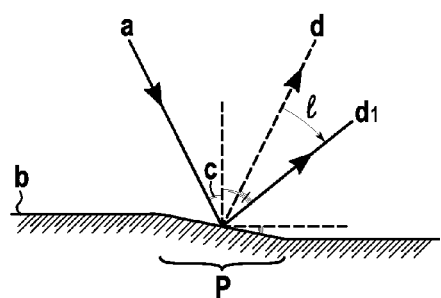
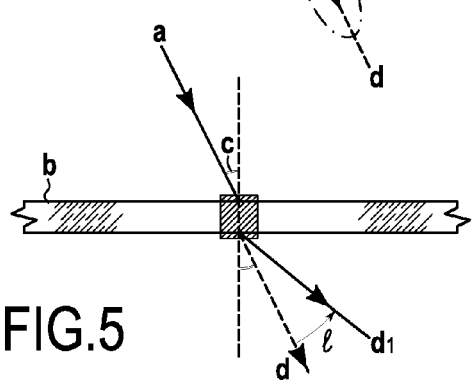
FIG.4         FIG.5

OPTICAL DEVICE FOR OBSERVING MILLIMETRIC OR SUBMILLIMETRIC STRUCTURAL DETAILS OF AN OBJECT WITH SPECULAR BEHAVIOUR

This application is a National Phase of PCT/EP2008/064683, filed on Oct. 29, 2008, which claims priority of FR 0758664, filed on Oct. 29, 2007, and U.S. Provisional Application No. 61/006,441, filed on Jan. 14, 2008.

The present invention concerns a device for the observation of an object in the general sense which, at a certain scale, possesses an optical behaviour that is not only diffusing or scattering, but also at least partially specular.

The present invention more particularly concerns a device that is designed for observing and measuring the surface state of an object, at millimetric or submillimetric resolution, especially in wide field, meaning where the viewing angle of the cone of light rays received by the observation system is large.

The invention finds particularly advantageous application in the observation of a surface of a flat or curved character, and of a reflecting nature, made of metal, plastic, glass, shellac, etc.

The present invention can thus be used for the inspection of surfaces in order to detect defects in objects, to characterise surfaces, to describe surface states (roughness), to perform surface cartography, to read information stored in the material, to extract data from the structure of the material, etc.

In the prior art, different solutions have been proposed to observe a surface displaying specular behaviour.

For example, for the detection of surface defects, patent application FR 2285990 proposes to illuminate the surface of an object, so as to create, by reflection, zones that are relatively distinct in dark and light (fringing), and to move these fringes on the surface to be inspected.

The patent also proposed to capture the images of the dark or light zones, so as to detect, in the captured image, light patterns in the dark zones or of the dark patterns in the light zones, in order to deduce from these the presence of a defect.

In like manner, patent application FR 2817042 proposed a device for examining a specular surface of a substrate with a shape like a curved glass pane. The document describes a method that consists of taking an instantaneous picture of a test card whose pattern is deformed in at least one direction, allowing one to determine the presence of defects on the surface of the substrate.

The technique starts from the observation of a specular material by measuring the deformation of a coding image based on fringes, and has a spatial resolution that is limited by the quality and the quantity of the fringes in the coding image. Moreover, the technique requires significant digital processing which leaves one with uncertainties regarding the shadow areas or the reliefs, frequently leading to interpretation errors.

Other techniques increase the number of acquisitions by the use of several sensors and/or several successive acquisitions, such as stereoscopic or polarimetric techniques. Furthermore, other techniques such as phase contrast imaging or strioscopy, are difficult or even impossible to implement for certain industrial applications, because of their sensitivity or of certain technical limitations in the topology of their constitution.

In the prior art, we are also familiar, through documents US 2003/026475 and US 2002/001029 for example, with optical devices for the observation of objects by virtue of the diffuse reflection of light and then the creation of dark and light areas (fringes) by reflection. However in order to present a reconstituted image, these devices require significant and complex digital processing.

The subject of the invention therefore aims to remedy the aforementioned drawbacks, by proposing a new device for the observation, by reflection, of the millimetric or submillimetric structural details of an object with specular behaviour, which is simple to implement, while also offering high resolution and being capable of functioning in wide field applications.

Another subject of the invention aims to propose a new observation device that is designed from standard optical elements, exhibiting a robustness and a compactness that is suitable for an industrial environment, especially for observation at high speed, while also offering the advantage of limiting or eliminating all digital processing.

In order to attain such an objective, the device for the observation by reflection of millimetric or submillimetric structural details in an object exhibiting a behaviour that is at least partially specular and located in an exposure area, is characterised in that it includes:
  at least one radiation source with a real or virtual emission surface that possesses at least two distinct regions emitting streams of radiation, in which at least one of the characteristics differs from one region to the next,
  an optical projection system that is located in line with the radiation source in relation to the exposure zone, in the path of the radiation, where this optical projection system includes an entry aperture,
  an optical exposure system positioned between the radiation source and the exposure zone, and designed to optically link the entry aperture of the optical projection system and the emission surface of the radiation source,
  a projection surface located in line with the exposure zone in relation to the optical projection system, and that is linked optically with the object in the exposure zone, and whose received radiation depends on the deflection from the object.

According to one application of the subject of the invention, the device includes localised detection means that are used, with the aid of the projection surface, to measure a value that corresponds to a value of ray deflection by the object.

According to one embodiment, the emission surface is of small dimensions and close to a point source, and the optical projection system with its diaphragm is the only element blocking the rays and located between the object and the projection surface.

The projection surface is advantageously designed to be sensitive to the type of radiation of the radiation source, and is associated with an electronic or optical processing system.

According to one embodiment, the radiation source emits visible and/or ultraviolet and/or infrared light radiation.

According to another embodiment, the radiation source emits sound waves, particles or electromagnetic waves.

According to one advantageous implementation characteristic, the emission surface has an image with at least two regions exhibiting different intensities and/or colours and/or polarisations separated by a transition region, formed by a line of separation or a gradual transition zone.

As an example, the emission surface includes a dark region and a bright region.

According to one embodiment, the emission surface of the radiation source is located in a virtual surface, by the use of special materials such as honeycombs and holograms for the radiation source.

According to another embodiment, the emission surface of the radiation source is located at infinity, and the optical exposure system links infinity with the entry aperture of the optical projection system.

According to another characteristic, the optical exposure system consists of the positioning and/or the adjustment of the object and/or of the emission surface with the entry aperture of the optical projection system, without the addition of supplementary optical elements.

According to one implementation example, the device includes a box inside which are integrated, in particular, the emission surface and a semi-reflecting plate, and in which the optical exposure system includes a cylindrical lens, in particular of the Fresnel type.

Advantageously, the device includes means for adjusting the position, on the optical axis, of the emission surface and/or of the lens and/or of the angle presented by the semi-reflecting plate or sheet.

According to one preferred application example, the device includes means for receiving a set of the deflection values, in order to extract the structural characteristics of the object corresponding to a signature of the object for example.

Advantageously, the means for receiving the values of deflections to extract a signature of the object are connected to a secure object tracing system.

Various other characteristics will emerge from the description provided below with reference to the appended drawings which show, by way of non-limiting examples, different forms of implementation of the subject of the invention.

FIGS. 1 and 1A illustrate the principle of an observation device in transmission, without and with deflection respectively.

FIGS. 2 and 3 are diagrams illustrating diffusing and specular behaviour without deflection of an object, respectively in reflection and in transmission.

FIGS. 4 and 5 are diagrams illustrating diffusing and specular behaviour with deflection of an object, respectively in reflection and in transmission.

Figure 6:
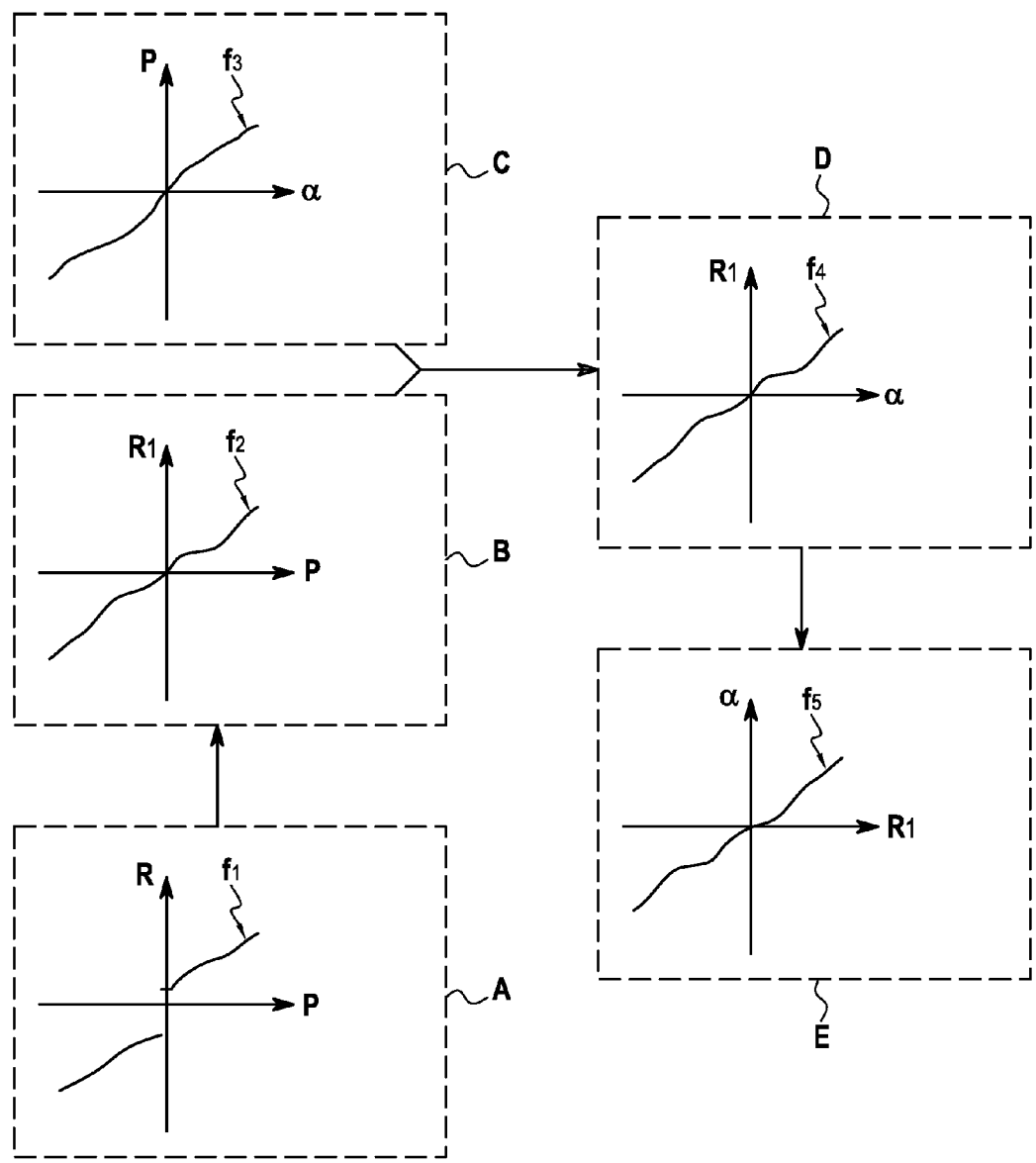

FIG. 6 includes graphs illustrating the transitivity of the transfer functions employed by the observation device according to the invention.

FIGS. 7A to 7E illustrate diverse variants of implementation of the radiation source.

FIGS. 8A to 8D illustrate diverse variants of implementation of the radiation source whose emission surface is virtual.

Figure 9:
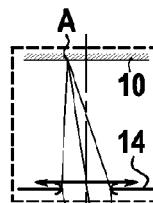

FIG. 9 is a schematic diagram of an observation device according to the invention, in reflection.

Figure 10:
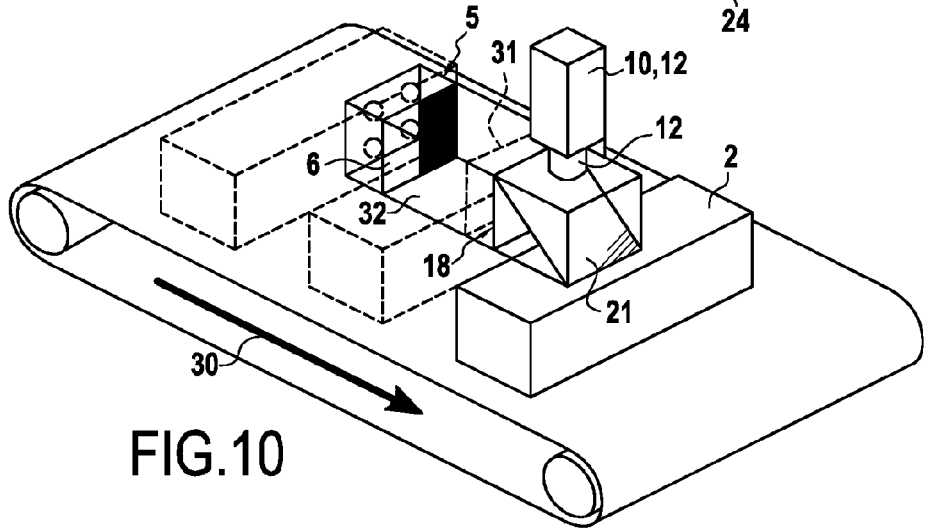

FIG. 10 is a view of one embodiment of an observation device according to the invention.

Figure 11:
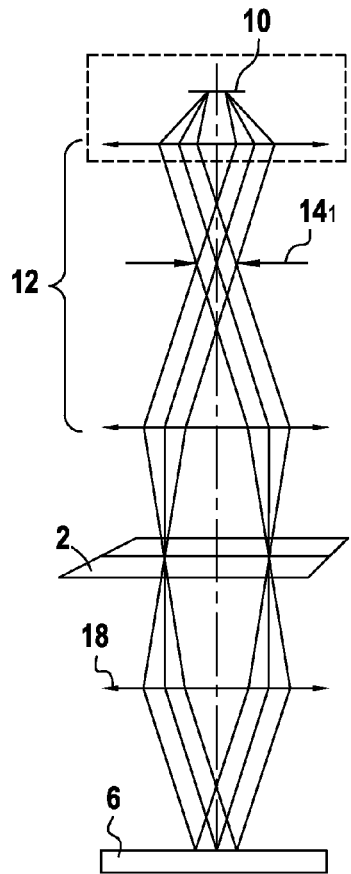

FIG. 11 is a view of another embodiment of an observation device using a telecentric lens.

Figure 12:
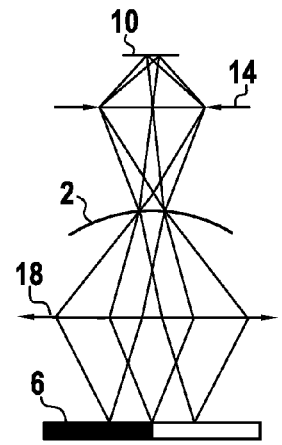

FIG. 12 is a view of another embodiment of an observation device according to the invention for curved surfaces.

Figure 13:
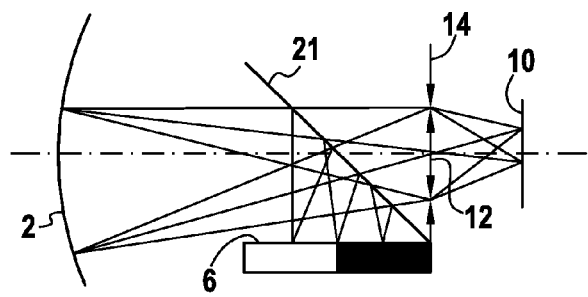

FIG. 13 is a view of another embodiment of a device according to the invention for the observation of defects in mirrors.

Figure 14:
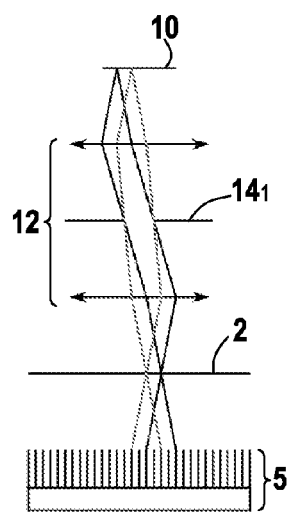
Figure 15A:
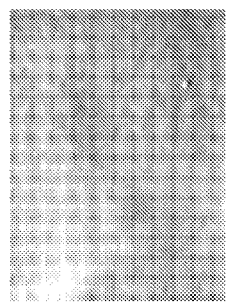
Figure 15B:
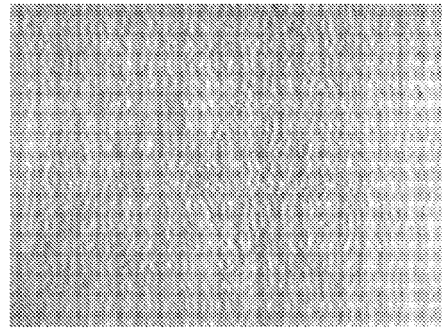
Figure 15C:
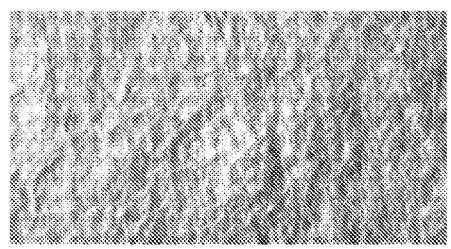
Figure 15D:
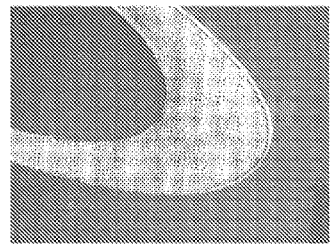
Figure 15E:
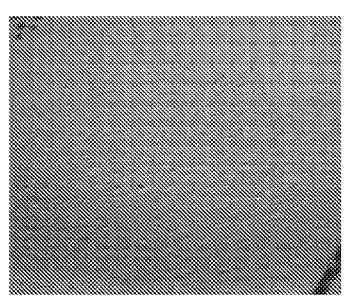
Figure 15F:
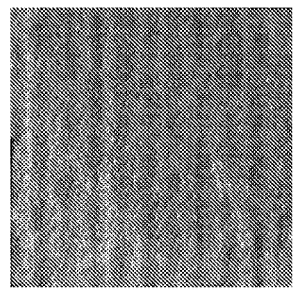

FIG. 14 is a view of an embodiment of an observation device whose optical exposure system has no lenses and which is using a telecentric lens associated with a honeycomb source.

FIGS. 15A to 15F are images of different objects, obtained with the observation device according to the invention.

FIG. 1 illustrates a device (1) that is designed to observe millimetric or submillimetric structural details of an object (2) exhibiting a behaviour that is at least partially specular, and placed in an exposure zone (3).

It must be understood that the term "object" can apply to any material or physical or informational phenomenon located in a zone of space and time. By "object", one can understand the surface of an object for example, such as a plate or sheet or laminar flow and its evolution in time, or the information contained in a medium. The subject of the invention more particularly concerns implementations of the device (1) allowing one to observe, by surface reflection, for example, the surface state of a plastified card, of a glass bottle, screen printing, etching or pad printing, or of the magnetic strip on a smartcard.

The observation device (1), which conventionally has an optical axis x, includes a radiation source (5) that is used for observation of the object (2) by means of an optical environment in the general sense. The radiation source (5) can supply a stream of electromagnetic radiation, not only at visible and/or ultraviolet and/or infrared wavelengths, but also all of the radiometric (electromagnetic) radiation wavelengths, of pressure waves (sound, infrasound (sub-audio), ultrasound, etc.) or particle streams (ions, electrons, molecules, etc.). The term "optical environment" is interpreted in the broad sense, meaning in all the areas for which the possibility of focussing exists, which includes electromagnetic waves (radiometry and optical lenses/mirrors, magnetic lenses, etc.), pressure waves (acoustic and acoustic lenses/mirrors, etc.), particle streams (with electromagnetic properties, mass properties, etc.), where this radiation is either coherent or incoherent.

It is recalled that when a ray or beam strikes an object, it potentially divides into multiple rays that emerge in various directions, whose intensity varies with the emergence direction, according to a transfer function. In the reflected and transmitted parts respectively, this transfer function can be considered as the sum of two functions, namely a transfer function of the specular part and a transfer function of the diffuse or scattered part of the reflection or of the transmission.

FIG. 2 illustrates the diffusing and specular behaviour of an object in reflection. As illustrated in FIG. 2, the incident ray (a) has formed an incidence angle (c) with the locally flat surface (b) of an object. The principal emergence mode of the reflected rays d forms a principal emergence angle (e) of the reflection, equal to the incidence angle (c) of the incident ray, in relation to the normal at the point of incidence. This diagram shows the angular transfer function (f) of the diffuse part of the reflection for the incidence angle (c), the angular transfer function (i) of the specular part of the reflection for the incidence angle (c), and the angular transfer function (k) of the reflection for the incidence angle (c).

The diffusing and specular behaviour in reflection can be transposed to the diffusing and specular behaviour in transmission. The transfer function breaks down into a diffused part in diverse directions, and a principal emergence mode, whose direction is unchanged in principle, if the faces of the object are locally parallel and if the object is locally homogenous. FIG. 3 illustrates the diffusing and specular behaviour in transmission for a translucent object (b), which is locally homogenous and locally has parallel faces. The incident ray (a) forms an incidence angle (c). The principal emergence mode of the transmitted waves (d) forms a principal emergence angle (e) of the transmission, equal to the incidence angle (c) of the incident ray. This FIG. 3 shows the angular transfer function (f) of the diffuse part of the transmission for the incidence angle (c), the angular transfer function (i) of the specular part of the transmission for the incidence angle (c), and the angular transfer function (k) of the transmission for the incidence angle.

It also appears necessary, for the remainder of the description, to define the deflection of a ray in reflection or in transmission. When, at the point of incidence of a ray, an object presents a flatness defect or an inhomogeneosity, its principal emergence mode can be deflected in relation to the behaviour that is expected in its absence. This deviation, which is called induced deflection, gives the impression to the observer that the ray is coming from another direction. FIG. 4 is a diagram illustrating the deflection of an incident ray (a) in reflection. The incident ray (a) presents an incidence angle (c) in relation to the normal at the point of incidence of the object (b), which has a flatness defect or an inhomogeneity (p). The principal reflection emergence mode (d1) with the flatness defect is deflected on a deflection angle (l) in relation to the behaviour that is expected (d) in its absence. In reflection, the deflection comes, in principle, from the flatness defect, but there can exist other reasons for deflection, such as the presence of a network of striations on the surface for example.

FIG. 5 illustrates the deflection diagram of an incident ray (a) in transmission, exhibiting an incidence angle (c) in relation to the normal to the plane of the object (b). In the case of a deflection in transmission, there appears a principal transmission mode ($d_1$) that presents a deflection angle (l) in relation to the principal transmission mode (d) that is expected with no defect in the object. In transmission, this deflection arises from characteristics of the structure of the object, such as a variable thickness (faces of the object not parallel) or from inhomogeneosities in the optical index for example.

It should be noted that FIG. 1 illustrates the principle of the observation device (1) in transmission and without deflection. The observation device (1) includes the radiation source (5) with an emission surface (6) diffusing the radiation from the source. By the use of a special optical device, the emission surface (6) can be in a real or virtual surface. This radiation source (5) is designed so that the emission surface (6) has at least two distinct regions (8, 9), emitting streams of radiation where at least one of the characteristics differs from one region to the next. As will be explained in detail in the remainder of the description, the emission surface (6) includes regions exhibiting as different characteristics, the intensity, the polarisation or the colour (using the L*a*b* colour model for example). It must be understood that the emission surface (6) thus presents a figure that is matched to the desired observation typology.

The device (1) also includes a projection surface (10) that constitutes a surface on which is formed the image of the object (2) observed by the device. This projection surface (10) corresponds, for example, to the retina of an eye of an observer, to a screen or to a radiation sensor (a camera for example) connected to an acquisition and processing unit. This projection surface (10) is matched to the nature of the radiation from the source (5) and is located in a darkened chamber (11).

The projection of the image onto the surface (10) is effected by an optical projection system (12) located in the path of the radiation, in line with the radiation source (5) in relation to the exposure zone (3). This optical projection system (12) includes an entry aperture (14). This entry aperture (14) is defined by the presence of a diaphragm forming part of the optical projection system (12) (the diaphragm of a lens in a camera for example). Conventionally, this diaphragm has a shape that allows rays to pass through its centre. It should be noted that this diaphragm is the only effective obscuring element present between the object (2) and the projection surface (10). In the interests of simplification in relation to the presentation in principle of the device, the optical projection system (12) has been reduced to a simple lens that is limited spatially by its physical dimensions, forming the aperture diaphragm. This is use in FIGS. 1, 8, 9, 12 and 13. It should be noted that the projection surface (10) is located in line with the exposure zone (3) in relation to the optical projection system (12). Such a projection surface (10) is linked optically with the object (2) in the exposure zone (3).

The observation device (1) also includes an optical exposure system (18) that is positioned between the radiation source (5) and the exposure zone (3). This optical exposure system (18) is designed to optically link the entry aperture (14) of the optical projection system (12) and the emission surface (6) of the radiation source. By way of an example, illustrated in FIG. 1, the optical exposure system (18) is chosen to be a lens in order to effect the link between the emission surface (6) and the entry aperture (14) of the optical projection system (12), this link being on a transverse axis or two transverse axes in relation to the optical axis x. However, as explained in the remainder of the description (FIG. 13), it can be arranged to create the link by adjusting the position and/or components between the emission surface (6) and the entry aperture (14).

The operation of the observation device (1) described above results directly from the preceding description. In this regard, instead of reasoning on the optical path followed by the rays emitted by a certain point of the radiation source, the principle is described for all of the optical paths that expose a point on the projection surface (10). The description of the operation of the observation device (1) is based on the principle of the inverted return of the light, and falls into the context of Gaussian approximation. In addition, the presentation of the principle is restricted here to one of the two transverse axes in relation to the optical axis. The principle can naturally be generalised to the two axes simultaneously.

For any point ($A_i$) on the projection surface (10) (namely $A_1$ and $A_2$ in FIG. 1), it is always the same zone (7) of the emission surface (6) of the radiation source (5) that is perceived. The emission surface (6) of the radiation source (5) diffuses in an isotropic manner, so that the projection surface (10) perceives a uniform illumination, indicating the absence of deflection.

FIG. 1A illustrates an example of an object (2) that is exhibiting an inhomogeneosity leading to a deflection (19) whose origin is recalled in the description relating to FIG. 5. Given a certain deflection angle, then whatever the point of the observed object (2), it is always the same zone (7) of the emission surface (6) that is perceived by a point ($A_i$) on the projection surface (10). However, this zone (7) on the emission surface, perceived with a deflection angle, differs from the zone (7) of the emission surface perceived in the absence of a deflection angle (FIG. 1). It appears therefore that there exists a unique relationship between the value of the deflection on the object and the position of the perceived zone (7) on the emission surface.

In the light of this unique relationship, it is arranged to cause a characteristic of the radiation diffused by the emission surface (6) (its intensity, its colour, etc. for example) to vary in a unique manner in accordance with the spatial position of the perceived zone (7). By transitivity, there therefore exists a unique relationship between the value of the deflection on the object and the value of a characteristic of the emission perceived by the projection surface (10), independently of the point of the observed objects. The extent of the zone perceived by point ($A_i$) corresponds, to within an order of magnification, to the shape of the entry aperture (14) relating to the deflection due to the object at point (20). This shape is offset in a unique manner on the emission surface (6) according to the deflection at the observed point of the object. As a consequence, integration of the stream of radiation received by point $A_i$ corresponds to a smoothing of the figure presented on the emission surface (6). The transitivity of the functions can therefore be expressed in accordance with FIG. 6.

Graph A of FIG. 6 presents the above principle, restricting itself to one of the two transverse axes in relation to the optical axis x, and illustrates the evolution of the value of the radiation characteristic (R) on the emission surface (6) in accordance with its position (P) on the emission surface (6). This radiation characteristic (R) evolves according to one growth function ($f_1$).

Graph B of FIG. 6 illustrates the evolution of the value of the radiation characteristic ($R_1$) perceived by a point ($A_i$) on the projection surface (10), in accordance with the position (P) of the perceived zone (7) on the emission surface. In the light of the integration of the zone (7) perceived by the point ($A_i$) on the projection surface (10), there follows a smoothing of the function over all of the perceived zone, so that the value of the perceived radiation characteristic evolves according to a continuous function ($f_2$) that is strictly increasing in accordance with the position of the perceived zone.

Graph C of FIG. 6 shows the evolution of the position (P) of the perceived zone according to the deflection angle ($\alpha$). This is a strictly increasing continuous function ($f_3$) which can be rendered close to an affine or linear function by adjusting the parameters (diffused figure, for example).

Through the composition functions of graphs B and C, we obtain, as illustrated by graph D, the evolution of the value of the radiation characteristic ($R_1$) perceived by point ($A_i$) on the projection surface, according to the deflection angle ($\alpha$). This value of the radiation characteristic ($R_1$) evolves according to a strictly increasing continuous function ($f_4$).

Naturally, as illustrated by graph E, it is possible to obtain the reciprocal function ($f_5$) (strictly increasing continuous function), corresponding to the evolution of the deflection angle ($\alpha$) in accordance with the value of the radiation characteristic ($R_1$) on the emission surface perceived by a point on the projection surface.

From the preceding description it can be seen that there exists a direct relationship between the value of deflection angle ($\alpha$) and the position of the zone (7) perceived by point ($A_i$) on the projection surface (10). By associating a unique stream intensity with each perceived zone (7), each corresponding to a deflection angle ($\alpha$), it is possible to observe the relief on a reflecting object without ambiguity.

Such a device (1) allows a person to observe the relief on a surface of an object. According to one application in which the projection surface is a sensor for example, the device (1) includes localised detection means which, by use of the projection surface (10), allow one to measure a value that corresponds to a value of ray deflection by the object (2). The sensor is designed for the type of radiation diffused by the emission surface (6) and allows one to measure or to extract characteristics from the observed object that are proper to the latter.

It emerges from the description of the principle described in FIG. 6 that different variants are possible for the application of the preceding principle, regarding their choice of figures for the emission surface (6), with this choice being designed for a desired type of observation. It is recalled that there exists a unique relationship between the deflection and the position of the perceived zone in the space generated by the two transverse axes in relation to the optical axis x.

In the case where the emission surface (6) approaches a point source, the diaphragm (14) of the optical projection system (12) allows the rays to pass via its centre. By a point source is meant a source whose spatial extent is very small compared to the spatial extent of the observed field.

The variants to create the emission surface (6) include at least two distinct regions emitting streams of radiation with at least one of the characteristics different from one region to the next. A characteristic of the stream of radiation, can be different intensities and/or colours for example.

Figure 7A:
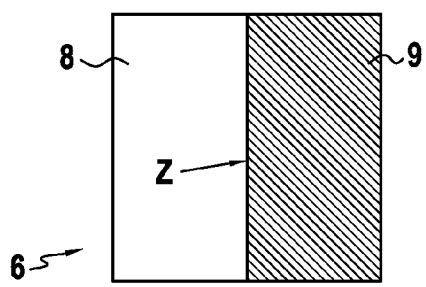
Figure 7C:
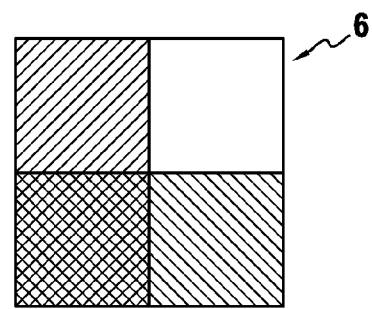
Figure 7B:
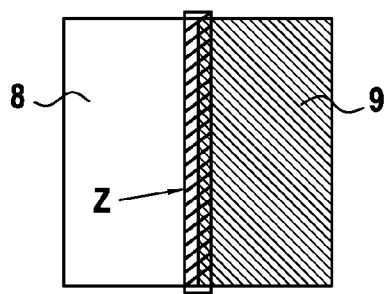

The examples illustrated in FIGS. 7A to 7B demonstrate a unique received deflection-intensity relationship on one of the two transverse axes to the x axis, independently of the deflection on the other transverse axis. According to these examples, the emission surface (6) includes a light or bright region (8) and a dark region (9), separated by a sharp rectilinear transition zone (Z) (FIG. 7A) or by a transition zone (Z) that is gradual or with a gentle gradient (FIG. 7B) (the intensity gradient).

Figure 7D:
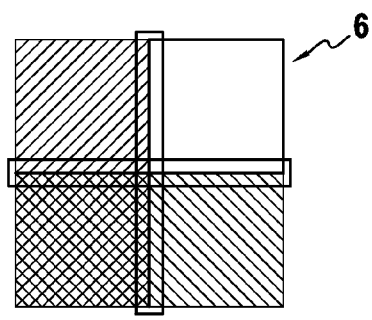

FIGS. 7C and 7D illustrate examples of implementation of an emission surface (6) exhibiting a received deflection-intensity relationship through a unique colour on each of the two axes transverse to the axis x, achieved by the superimposition of two vertically and horizontally orthogonal zones, each assigning a different colour (a red line with a green column for example). In the example illustrated in FIG. 7C, the regions are separated by a transition zone with a sharp limit, then in FIG. 7D, the regions are separated by a gradual transition zone.

Figure 7E:
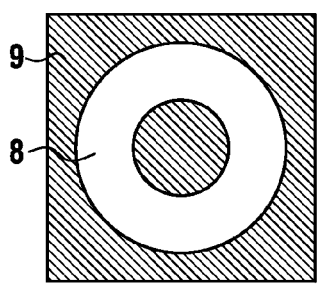

FIG. 7E illustrates an emission surface (6) with a concentric figure in the form of a bright annular zone on a dark background allowing one to observe, on the object, the zones whose deflection angle in relation to the normal to the observed surface has a value that is determined independently of the direction of deflection in the observed surface.

In the previous examples, the radiation source (5) includes a real emission surface (6) diffusing the chosen pattern. This diffusing surface can be in the form of a substitution optical device by the creation of real or virtual images. FIGS. 8A to 8D present embodiments of this principle.

Figure 8A:
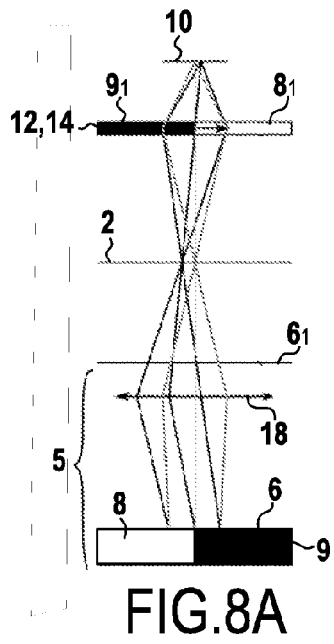

FIG. 8A illustrates an implementation variant using a hologram whose physical surface ($6_1$) simulates all of the functions employed by the optical exposure system (18) and the emission surface (6). Like the devices that it replaces, it generates a real image of an emission surface (6) in the plane of the entry aperture (14) of the optical projection system (12). Zones (8, 9) and ($8_1$, $9_1$) respectively illustrate the use of the example of a diffused figure in FIG. 7A, and formation of the real image corresponding to the simulation of lining up by a lens (18). Integration of the optical exposure system (18) into the hologram has the advantage of rendering the device more compact.

Figure 8C:
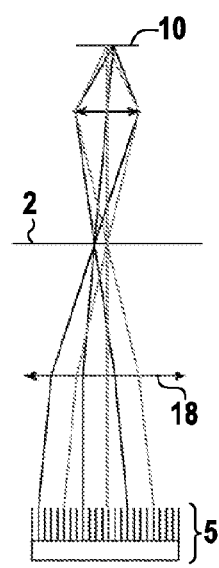
Figure 8D:
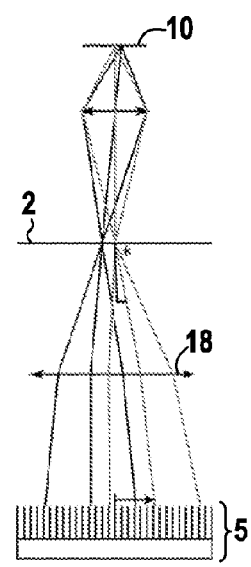
Figure 8B:
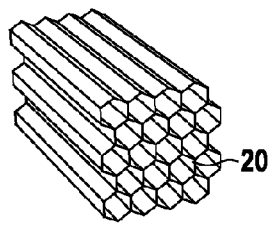

FIG. 8B presents an embodiment of a structure that allows one to approach collimation of the light. The example describes a honeycomb structure (20) extended along an axis, that is translucent at least on the axis and opaque when offset from this axis. The use of this honeycomb structure in front of a diffuse source (FIG. 8C) simulates a collimated source through the use of a lens (18) that is playing the role of the optical exposure system, by the connection of infinity with the entry aperture (14) of the optical projection system (12). In the presence of a deflection (FIG. 8D), the beam of the paths leading to point ($A_1$) is inclined in relation to the axis of the honeycomb structure so that the perceived intensity reduces.

In the example illustrated in FIGS. 1 and 1A, the device (1) is to perform observation in transmission. In accordance with the invention, the device (1) is designed to perform observation by reflection.

FIG. 9 illustrates an application example of a device (1) according to the invention used for observation by reflection employing a semi-reflecting plate (21) positioned on the optical path between the projection surface (10) and the object (2). FIG. 9 shows firstly all of the source paths (23) of the stream without deflection at a point (24) on the object (2) and secondly, all of the source paths (25) of the stream with deflection at point (24) on the object (2). Point (24) on the object (2) is therefore observed by point ($A_i$) on the projection surface (10), which perceives a zone (26) on the emission surface (6) without deflection at point (24), and a zone (27) of the emission surface that differs from zone (26) with deflection at point (24). The use by the emission surface of a diffused figure according to the methodology presented in the description of FIGS. 5 and 7A to 7E allows one to observe the deflection at point $A_i$.

FIG. 10 presents an embodiment of a device (1) for observation in reflection of the surface of objects (2) with characteristics that are not diffusing only, passing by means of a conveyor (30) in front of the observation device (1), which has as its radiation source (5) an emission surface (6) in the form of a diffusing element exhibiting a figure with a bright zone and a dark zone separated by a sharp vertical boundary. The emission surface (6) is illuminated in the example from the rear by a light source such as electroluminescent diodes. The emission surface (6) lies at a distance from an optical exposure system (18) in the form, for example, of a cylindrical Fresnel lens on a vertical axis. This Fresnel lens (18) is positioned between the emission surface (6) and the semi-reflecting plate (21), above which is placed the optical projection system (12) and the projection surface (10) forming part of a camera. The radiation source 5, the Fresnel lens (18), and the semi-reflecting plate (21) are mounted in a box (32) of relatively small size, on which the camera is fixed.

In the implementation, the addition of a cylindrical Fresnel lens (31) with a horizontal axis positioned between the emission surface (6) and the optical exposure system (18) is used to eliminate a vignetting phenomenon on the image perceived by the projection surface (10).

According to a preferred implementation characteristic, the observation device (1) includes means for adjusting the position, on the optical axis x, of the emission surface (6) and/or of the Fresnel lens (18), and/or of the angle presented by the semi-reflecting plate (21) in relation to either or both of the transverse axes in relation to the optical axis x. These adjustment means can be of a manual or automated nature, possibly in a control loop, and can, for example, be used to adjust the device to an incorrect presentation of the observed object (2).

FIG. 10 describes an implementation of the device (1) according to the invention for observation by reflection. It should be noted that the use of a semi-reflecting plate (21) does not limit the invention in any way. In general, one can envisage creating the component elements of the device (1) in different ways, while still allowing the same type of observation.

For example, FIG. 11 illustrates the optically unfolded diagram of an observation device (1) in reflection, using as its optical projection system (12), a telecentric lens on the object side. According to this embodiment, the entry aperture (14) is formed by the iris ($14_1$) of the telecentric lens. It should be noted that the optical exposure system (18) is always chosen to optically link the entry aperture (14) of the optical projection system (12) and the emission surface (6) of the radiation source.

Such an implementation variant has the advantage in particular of eliminating image distortion, as well as observing objects whose deflection characteristics in reflection are dependent on the incidence angle.

FIG. 12 presents the optically unfolded diagram of a device (1) that is designed more particularly for observing curved surfaces that result in a large dynamic range of the deflection angle. As can be seen in FIG. 12, the object (2), and in particular the observed surface, can be likened macroscopically to a supplementary optical system of the observation device (1). For example, the observed surface corresponds to the inside or outside of a cylinder or sphere. This surface can therefore be likened to a convergent or divergent cylindrical or spherical mirror. In this case, the optical exposure system (18) is designed to create the link between the emission surface (6) and the entry aperture (14) of the optical projection system (12), that is a virtual image. The image observed on the projection surface (10) is neutral for an object with no defect, which behaves as the equivalent optical system.

FIG. 13 illustrates an application example of the principle illustrated in FIG. 12, for the observation of defects appearing on a mirror such as that of a telescope. According to this embodiment, the optical exposure system (18) consists of positioning the optical elements so as to make the link between the emission surface (6) and the entry aperture (14). This is the concave mirror (2) that effects the connection between the emission surface (6) and the entry aperture (14). In the implementation of this example, a reflecting plate (21) is positioned between the projection surface (10) and the object (2).

FIG. 14 illustrates an optically unfolded diagram of another implementation variant of an observation device (1) that combines the optical elements introduced in the variants illustrated in FIGS. 8C, 8D and 11, meaning a honeycomb structure associated with a telecentric lens. This variant includes an optical exposure system (18) with no lenses. In other words, this combination can be used to make the connection that has to be effected by the optical exposure system (18), without the addition of extra optical components. In fact this type of radiation source (5) located the emission surface (6) at infinity, while the entry element of the telecentric lens puts the entry aperture of the optical projection system (12), determined by iris ($14_1$), at infinity also, with the connection made by the optical exposure system (18) being thus achieved.

Whatever the implementation method or embodiment, the observation device (1) allows one to observe the relief on objects of diverse natures, and to acquire images that are particularly rich in information. FIG. 15A to 15F illustrate diverse images obtained by the observation device (1), respectively for a surface in clear glass (FIG. 15 A) or coloured glass (flasks, bottles, windows, etc.), whether screen printed or not, or pad printed or not, a card surface (layered or plastified card, packing cases whether complex or not, silvered laquered card boxes FIG. 15 B, gilt imprinted box (FIG. 15 C), a plastic surface with printing, metallised or not, printed transparent self-stick plastic labels (FIG. 15 D), a safety hologram with metallised plastic support (FIG. 15 E), or a metallic surface such as, for example, the surface of a magnetic strip on a smartcard (FIG. 15 F).

The observation device (1) is designed to observe any surface that is specular at least, and in particular those for which the diffusing techniques do not produce a result— liquids, gases with specular behaviour, variable field on a surface or a volume, surfaces with holographic behaviour, multi-scale structures, transparent plates with variable indices, inert or living objects, etc.

The object of the invention finds many applications, such as optical metrology, certification of surface states (roughness, surface characterisation, surface appearance, surface identification, surface cartography, geometrical tolerance, reading of stored information, parallel reading (increasing the flow) of stored information, extraction of structures for authentication methods, coding of information, and in particular the operations described in patent applications FR 2 866 139, WO 2005/76651, US 2005/2622350, FR 2 870 376, FR 0513231 and FR 0601342, the extraction of data for biometry, sophistication of sonars and radars, electronic microscopes, etc.).

The observation device (1) has many advantages in relation to the competing techniques:

its low cost: by the use of simple and standard, and therefore inexpensive optical components, the cost of such a device is low.

its simplicity
of assembly and adjustment, and its compactness: the adjustment of such a device is not very sensitive in comparison to most of the other devices. The number of components is reduced and the optical path is relatively short, thus rendering it compact, and reducing the complexity of assembly and adjustment.

by a reduced numerical calculation, autonomy of the system is achieved—it is no longer necessary to effect pre-processing for the reconstitution of information (as with systems that use the deformation of a pattern, employing stages of phase detection or intercorrelation calculations, amongst other things), observation or measurement of the object can be direct, either through direct viewing by an operator, or making use of the acquired values. Moreover, the correct operation of the system requires no supervision, which can be necessary to other systems in order resolve indeterminates (for phase realignment, etc. for example).

effectiveness: since any calculation stage is reduced, and with only one acquisition being necessary, it is possible, with the same components, to observe, continuously and even as high speed, with the limiting factor being the rate of acquisition of the sensor. Measurement is "full resolution": information is acquired by measurement, where other systems must interpolate after the information has been reconstituted. In addition, the observed field can be wide in relation to the size of the whole device. This system is not based on a measurement scan (a laser scan for example), so all of the acquisitions can be synchronous, and this can be critical for applications whose observation must effected at high speed (for observing a very rapid phenomenon for example).

robustness: adjustment is not very sensitive. According to the principle of the invention, the smoothing effected by the integration of the received stream can be used to stabilise the measurement in relation to defects in the components and/or the adjustments, where certain systems are sensitive to the smallest irregularity (irregularity of the fringe pattern for a system that is based on their deformation, etc.). This robustness also allows the use of systems with no quality imaging quality, so that the use of Fresnel lenses for the optical exposure system (18) is possible. Since the principle of the invention is not based on interference phenomena, it does not suffer from the same sensitivities as those with a variety of parasitic factors. In systems employing fringing, a correspondence is sought between an entire region of the acquired image and a region of the emission surface. Conversely, according to the invention, for each pixel of the acquired image, the value perceived corresponds to a position in the transition zone between the regions, and therefore to an angular deflection value, independently of the position of the pixel in the image.

versatility: it is possible to observe a very wide class of objects, with different types of radiation.

extension potential: by the choice of diversity for the coding types, the measurement typology can be very varied, and there is also considerable freedom in the choice of the optical components used.

The invention claimed is:

1. An acquisition device for the observation, by reflection, of millimetric or submillimetric structural details of an object (2), exhibiting a behaviour that is at least partially specular, located in an exposure zone (3), characterised in that the device includes:

at least one radiation source (5) with a real or virtual emission surface (6) that possesses at least two distinct regions (8, 9) emitting streams of radiation, where at least one of the characteristics differs from one region to the next, an optical projection system (12) that is located in opposed position with the at least one radiation source in relation to an exposure zone, in the path of the radiation issuing from the at least one radiation source (5), where this optical projection system (12) includes an entry aperture (14), an optical exposure system (18) positioned between the at least one radiation source (5) and the exposure zone (3) and configured to optically conjugate the entry aperture (14) of the optical projection system (12) and the emission surface (6) of the at least one radiation source, the optical conjugation of the entry aperture (14) and the optical projection system (12) meaning that different rays issued from a same point of the emission surface (6) and having different directions intersect at the same point at the entry aperture (14), a projection surface (10) located in opposed position with the exposure zone (3) in relation to the optical projection system (12), the optical projection system (12) including at least one lens for another optical conjugation, which optically conjugates the projection surface (10) with the object in the exposure zone (3), the another optical conjugation of the projection surface (10) with the object in the exposure zone (3) meaning that different rays issued from a same point of the object (2) and having different directions intersect at the same point at the projection surface (10).

2. An acquisition device according to claim 1, characterised in that the acquisition device includes localized detection means that are used, by means on the projection surface (10), to measure a value that corresponds to a value of ray deflection by the object (2).

3. An acquisition device according to claim 1, characterised in that the emission surface (6) approximates a size of a point source, and in that a diaphragm (14) of the optical projection system (12) is the only element that blocks the rays, located between the object (2) and the projection surface (10).

4. An acquisition device according to claim 1, characterised in that the projection surface (10) is designed to be sensitive to the type of radiation of the at least one radiation source (5), and is associated with an electronic or optical processing system.

5. An acquisition device according to claim 1, characterised in that the at least one radiation source (5) emits a bright radiation that is one of visible, ultraviolet, and infrared or a combination thereof.

6. An acquisition device according to claim 1, characterised in that the at least one radiation source (5) emits sound waves, particles or electromagnetic waves.

7. An acquisition device according to claim 1, characterised in that the emission surface (6) presents a figure with at least two regions (8, 9) exhibiting at least one of different intensities, colors, and polarizations, separated by a transition region (Z), defined by a line of separation or a gradual transition zone.

8. An acquisition device according to claim 7, characterised in that the emission surface (6) includes a dark region (9) and a bright region (8).

9. An acquisition device according to claim 1, characterised in that the emission surface (6) of the at least one radiation source (5) is located in a virtual surface, by the use of at least one of honeycombs and holograms for the at least one radiation source (5).

10. An acquisition device according to claim 1, characterised in that the emission surface (6) of the at least one radiation source (5) is located at infinity, and that the optical exposure system (18) links infinity with the entry aperture (14) of the optical projection system (12).

11. An acquisition device according to claim 1, characterised in that the optical exposure system (18) consists of one or both of positioning or adjusting one or both of the object (2) and the emission surface (6) with the entry aperture (14) of the optical projection system (12), without the addition of extra optical elements.

12. An acquisition device according to claim 1, characterised in that the acquisition device includes a box (32) inside which are integrated in particular the emission surface (6) and a semi-reflecting plate (21), and the optical exposure system (18) includes a cylindrical lens.

13. An acquisition device according to claim 12, characterised in that the cylindrical lens is a Fresnel type lens.

14. An acquisition device according to claim 1, characterised in that the acquisition device is adapted to adjust the position, on the optical axis (x), of at least one of the emission surface (6), a lens, and the angle presented by a semi-reflecting plate (21).

15. An acquisition device according to claim 1, characterised in that the acquisition device is adapted to receive a set of values of deflections, in order to extract structural characteristics of the object.

16. An acquisition device according to claim 15, further comprising an object tracing system that permits extracting a signature of the object based on the received values of rendered deflection.

17. An acquisition device according to claim 1, characterised in that the structural characteristics of the object correspond to a signature of the object.

* * * * *